United States Patent [19]

Bunger et al.

[11] 4,126,755
[45] Nov. 21, 1978

[54] PROCESS FOR THE PREPARATION OF DIMETHYL TEREPHTHALATE

[75] Inventors: Heinrich Bunger, Witten-Bommern, Germany; Otto W. Bleh, deceased, late of Troisdorf-Bergheim, Germany, by Rita M. Bleh, heiress

[73] Assignee: Dynamit Nobel Aktiengesellschaft, Germany

[21] Appl. No.: 396,468

[22] Filed: Sep. 12, 1973

[30] Foreign Application Priority Data

Sep. 12, 1972 [DE] Fed. Rep. of Germany ....... 2244662

[51] Int. Cl.$^2$ ............................................. C07C 69/82
[52] U.S. Cl. .......................................... 560/77; 560/78
[58] Field of Search ....................... 260/475 R, 475 B; 560/77, 78

[56] References Cited

U.S. PATENT DOCUMENTS

| 2,773,090 | 12/1956 | Leibu ................................. 260/475 B |
| 3,248,417 | 4/1966 | Hoffmann et al. .................. 260/475 |
| 3,277,153 | 10/1966 | Pieroh ................................. 260/475 |

FOREIGN PATENT DOCUMENTS 46-6,412  2/1971  Japan ................................... 260/475 B Primary Examiner—Jane S. Myers
Attorney, Agent, or Firm—Craig & Antonelli

[57] ABSTRACT

A process for producing dimethyl terephthalate from high-boiling tarry residues from the combined oxidation of p-xylene and p-toluate in the liquid phase, esterification of the resulting acids with methanol and separation of the resulting dimethyl terephthalate which include the steps of subjecting the high-boiling residues to treatment with methanol at temperatures above 250° C. and thereafter separating the resulting dimethyl terephthalate in accordance with conventional separation techniques.

6 Claims, No Drawings

PROCESS FOR THE PREPARATION OF DIMETHYL TEREPHTHALATE

This invention relates to a process for the preparation of dimethyl terephthalate involving the utilization of high-boiling tarry residues obtained in conventional processes for the production of dimethyl terephthalate by the common i.e. combined, oxidation of p-xylene and p-toluic acid ester, by subsequent esterification of the thus-obtained acids, and by separation of dimethyl terephthalate and more particularly, a process wherein such residues are treated with methanol.

In the large-scale technical production of dimethyl terephthalate in accordance with the aforementioned conventional processes, (which are disclosed for example in U.S. Pat. No. 2,894,978), appreciable amounts of high-boiling by-products occur, which accumulate as residues. Consequently, a process making it possible to convert these by-products economically and in satisfactory yields also into dimethyl terephthalate (required as a raw material for synthetic fibers and films) has great technical significance. These high-boiling by-products consist of a mixture of organic acids, esters, alcohols, and aldehydes of a complicated composition.

It is known from German Pat. No. 1,142,858 that "varying amounts" of dimethyl terephthalate and dimethyl isophthalate can be obtained by the secondary esterification of such a high-boiling mixture with methanol for the purpose of producing and isolating methyl esters of diphenylcarboxylic acid at 250° C. in an autoclave and by subsequent distillation under vacuum. However, this mode of operation, if employed for the production of dimethyl terephthalate, has several disadvantages. On the one hand, the yields of dimethyl terephthalate are greatly dependent on the distillation conditions to which the high-boiling tarry by-products are subjected prior to and after the methanol treatment. For example, if such low-volatile by-products are treated at 250° C. with methanol and then distilled under vacuum, reactions take place during the distillation, by which the dimethyl terephthalate is again partially converted into undesirable low-volatile substances. Another disadvantage is that additional by-products are obtained during this treatment which, when recycled into the common oxidation stage, strongly inhibit the oxidation of p-xylene and/or methyl p-toluate. However, this phenomenon does not involve the known inhibiting effect of toluyl alcohol, for this compound cannot be detected by gas chromatography. The aforementioned unknown by-products which act as inhibiting impurities are also produced if the methanol-treated high-boiling mixture no longer contains p-toluyl-p-toluate. They are enriched in the mother liquor of the recrystallization stage of dimethyl terephthalate. Thus the recycling of the residue of this mother liquor, obtained by evaporation, into an oxidation stage of the dimethyl terephthalate production results in a reduced oxidizing rate. The evaporation-derived residue must, therefore, either be discarded, although it still contains quantities of dimethyl terephthalate and methyl p-toluate essential to the economy of the process; or it must be subjected to an expensive purification step prior to recycling, alternatively, reduced oxidizing rates had to be tolerated.

The mode of operation according to the process of this invention eliminates these disadvantages. The aftertreatment according to this invention with the use of methanol can be accomplished with such low-volatile, i.e. high boiling, by-products of the dimethyl terephthalate production, which by-products have already been subjected to special secondary evaporation or re-evaporation. These by-products, depending on the thoroughness of the evaporation treatment, usually do not contain any amounts of p-toluyl-p-toluate detectable by gas chromatography, (trace amounts may be detectable by particularly sensitive analysis) and the acid number of such by-products is below 30 mg. KOH/g. The process can also be carried out just as advantageously with the low-volatile by-products that are obtained, without the use of any special secondary evaporators, or re-evaporators in a customary vacuum distillation of crude dimethyl terephthalate in a column.

The aftertreatment with methanol in accordance with the present invention requires no catalyst; however, it is also possible to conduct the process in the presence of the conventional esterification and interesterification catalysts. Advantageously, the aftertreatment is effected continuously at temperatures substantially above 250° C. (i.e. not less than 270° C.) under elevated pressure in columns or reactor vessels. Pressures of from about 5 to about 80 atmospheres gauge, more preferably between 10 and 50 atmospheres gauge, may be utilized and temperatures of from about 275° C. to about 350° C. are particularly effective. The residence time of the low-volatile by-product to be reacted in the reactor must be adapted to the pressures employed, in order to obtain a sufficient conversion. In case of pressures of between about 10 and about 50 atmospheres gauge, the residence time is advantageously several hours, especially from about 0.3 to about 6 hours. The amount of methanol utilized, based on the amount of the low volatile, high-boiling, tarry by-products, can be varied within wide limits, i.e. from about 30 to about 500 parts of methanol per 100 parts of the high-boiling by-products.

A separating step following the methanol treatment according to this invention is suitably executed by evaporating the methanol followed by distillative fractionation under reduced pressure. This procedure which is advantageously carried out in a film evaporator separates the methanol treated by-products into a residue fraction and into a fraction containing predominantly dimethyl terephthalate and other compounds which can be converted into dimethyl terephthalate (DMT) after separation from the DMT upon recycling into the oxidation stage of the process. The main amount of dimethyl terephthalate is separated from the fraction containing predominantly dimethyl terephthalate suitably in a conventional manner by crystallization from methanol; the proportions soluble in methanol are advantageously obtained conventionally by evaporation of the mother liquor and are recycled into the oxidation stage of the process.

The advantages attainable by the present invention reside particularly in that the yields of the processes known theretofore for the production of dimethyl terephthalate are markedly improved, and that simultaneously the amounts of useless tarry by-products, which are customarily combusted, are reduced to about 60–75% of the previous amounts.

The process of this invention will be further understood from the following examples of its preferred embodiments.

EXAMPLE 1

Low-volatile tarry by-products obtained from the dimethyl terephthalate production by the common oxidation of p-xylene and methyl p-toluate such as disclosed in U.S. Pat. 2,894,978, which by-products had been extensively separated by distillation in reevaporators under vacuum, contained in accordance with gas-chromatographic analysis, 5.0% by weight of dimethyl terephthalate, less than 0.5% by weight of methyl p-toluate, and less than 0.5% by weight of p-toluyl-p-toluate. The acid number of the by-product mixture was 16.0 mg. KOH/g.

In an autoclave equipped with a control valve, 465 g. of methanol is pumped continuously within 4 hours through 100 g. of these low-volatile tarry by-products at 290° C. and under a pressure of 28 atmospheres gauge. Vapor-phase methanol was continuously discharged via the control valve, which opened at 28 atm. gauge, and after expansion to atmospheric pressure was condensed in a cooler. At the end of the four-hour experiment, the autoclave was expanded at 290° C. to atmospheric pressure with the aid of the control valve; the thus-vaporized methanol was likewise condensed. In total, 580 ml. of methanol condensate was obtained (i.e. 458 g.) The content of the autoclave was cooled after expansion and distilled discontinuously from a glass flask without a column. At 50 torr (mm. Hg) and a temperature which was gradually raised from 170° C. to 280° C., 40.8 g. of distillate and 62.2 g. of distillate residue were obtained. The acid number of the residue was 4.0 mg. KOH/g., and the content of dimethyl terephthalate therein, determined by gas chromatography, was 4.6% by weight.

An analysis of the amount of 40.8 g. of distillate by gas chromatography showed a content of 25.0 g. of dimethyl terephthalate, 3.5 g. of methyl p-toluate, and 0.9 g. of the methyl ester of terephthaladehydic acid.

From this distillate was separated 20.0 g. of dimethyl terephthalate by crystallization from methanol; the mother liquor of the crystallization was evaporated, toward the end at 100° C. and 200 torr, thus obtaining 23 g. of evaporation residue having an acid number of less than 1 mg. KOH/g.

8.0 g. of this evaporation residue was utilized in an oxidation experiment with 106 g. of p-xylene, 300 g. of methyl p-toluate, and 70 mg. of cobalt (in the form of cobalt (II) ethylhexanate). For this purpose, 0.8 liter of air per minute was passed through this mixture for six hours at 140° C. and 760 torr. The induction period until oxygen absorption by the mixture and the acid number of the mixture after 6 hours served as a measure of oxidizability. In the present example, the induction period was less than 5 minutes, and the acid number after 6 hours was 43.4 mg. KOH/g. thus showing a very good oxidizability.

EXAMPLE 2

An oxidation experiment was conducted as in Example 1, but with the difference that no evaporation residue was added to the mixture of 106 g. of p-xylene, 300 g. of methyl p-toluate, and 70 mg. of cobalt. The induction period was again less than 5 minutes, but the acid number after 6 hours was 37.0 mg. KOH/g. Thus, indicating a good oxidizability.

EXAMPLE 3

The mode of operation of Example 1 was repeated with 100 g. of the same low-volatile tarry by-products characterized in Example 1, with the only difference that the methanol treatment was effected at 250° C. rather than 290° C. In this case, only 28.1 g. of distillate was obtained, containing, as determined by gas-chromatographic analysis, 14.8 g. of dimethyl terephthalate, 2.5 g. of methyl p-toluate, and 0.5 g. of the methyl ester of terephthaladehydric acid. In the thus-produced 7.30 g. of distillation residue, 4.2% by weight of dimethyl terephthalate was determined to exist by gas chromatography.

An oxidation experiment with the addition of 8 g. of evaporation residue, analogously produced as in Example 1, resulted in this case in an induction period of more than 6 hours. The acid number of the product, after the six-hour treatment with air, was below 2.0 mg. KOH/g. The analysis of the evaporation residue by gas chromatography showed, in addition to dimethyl terephthalate, toluic acid methyl ester, and methyl ester of terephthaladehydic acid, several unidentifiable compounds, but no toluyl alcohol.

EXAMPLE 4

The mode of operation according to Example 3 was repeated, with the sole difference that the distillation was effected, after termination of the methanol treatment, continuously at 50 torr and 205° C. in a thin-film evaporation apparatus, rather than discontinuously from a flask. This time, 38.4 g. of distillate was obtained containing, as determined by gas-chromatographic analysis, 19.8 g. of dimethyl terephthalate, 2.9 g. of methyl p-toluate, and 0.3 g. of the methyl ester of terephthalaldehydic acid. 63.8 g. of distillation residue contained 3.6% by weight of dimethyl terephthalate.

An oxidation experiment with the addition of 8 g. of evaporation residue analogously to Example 1 resulted in an induction period of more than 6 hours. The acid number was measured to be 2.0 mg. KOH/g.

EXAMPLE 5

Prior to the methanol treatment, the cobalt was removed to an extent of less than 10 p.p.m. from the low-volatile tarry by-products of the type used in Example 1 by extraction with water at 90° C. After drying under vacuum at 90° C., 100 g. of these by-products with a low cobalt content was treated with methanol and worked up exactly as set forth in Example 1, thus obtaining 39.8 g. of a distillate containing 24.3 g. of dimethyl terephthalate, 3.7 g. of methyl p-toluate, and 1.1 g. of terephthalaldehydic ester. 61.7 g. of distillation residue with an acid number of 4.5 mg. KOH/g. contained 4.9% by weight of dimethyl terephthalate.

The recrystallization of the distillate from methanol resulted in 18.8 g. of dimethyl terephthalate and 22.2 g. of evaporation residue. An oxidation experiment analogously to Example 1 with the addition of 8.0 g. of evaporation residue showed an induction period of less than 5 minutes and an acid number, after six hours, of 42.0 mg. KOH/g.

EXAMPLE 6

100 g. of low-volatile tarry by-products from the production of dimethyl terephthalate with the use of a cobalt and manganese mixture as the oxidation catalyst contained 5.4% by weight of dimethyl terephthalate and less than, respectively, 0.5% by weight of methyl p-toluate and p-toluyl-p-toluate; the acid number was 19.4 mg. KOH/g.

When using the same amounts and conducting the process in the same manner as in Example 1, 42.3 g. of distillate was obtained containing 26.3 g. of dimethyl terephthalate, 3.8 g. of methyl toluate, and 1.2 g. of the methyl ester of terephthalaldehydic acid. After recrystallization from methanol and evaporation of the mother liquor, 24.1 g. of evaporation residue was produced. An oxidation experiment analogously to Example 1 resulted in an induction period of less than 5 minutes and, after 6 hours, in an acid number of 44.4 mg. KOH/g.

It will be appreciated that in the oxidation experiments in the foregoing examples, a higher acid number of the oxidation product means that a greater proportion of the initial compound was oxidized, i.e. the space-time yield of the oxidation is higher.

While the novel principles of the invention have been described, it will be understood that various omissions, modifications and changes in these principles may be made by one skilled in the art without departing from the spirit and scope of the invention.

What is claimed is:

1. A process for the production of dimethyl terephthalate from the high boiling tarry residues obtained after the combined air oxidation of p-xylene and methyl p-toluate in the liquid phase in the presence of an oxidation catalyst, esterification of the thus-produced acids with methanol, and separation of dimethyl terephthalate, which comprises subjecting the high boiling residues to a methanol treatment at a temperature of from 270° C. to about 350° C. and at pressures of from 5 to about 80 atmospheres gauge, the amount of methanol used being from about 30 to about 500 parts per 100 parts of the high boiling residues, and separating dimethyl terephthalate from the resultant product.

2. The process of claim 1, in which said dimethyl terephthalate is separated from said resultant product by evaporating methanol followed by distillative fractionation under reduced pressure wherein a residue fraction and a fraction containing predominantly dimethyl terephthalate and other compounds which can be converted into dimethyl terephthalate are produced, and by separating dimethyl terephthalate from said fraction containing predominantly dimethyl terephthalate by crystallization from methanol.

3. A process for producing dimethyl terephthalate according to claim 2, which further comprises evaporating the resultant mother liquor to obtain an evaporation residue soluble in methanol and recycling said residue to said air oxidation step.

4. The process of claim 1, further comprising, prior to said methanol treatment, pretreating said high boiling residues by subjecting said residues to an evaporative treatment whereby the residues do not contain any amounts of p-toluyl-p-toluate detectable by gas chromotography.

5. The process of claim 1, in which the high boiling residues are treated with methanol at temperatures of from 275° C. to about 350+ C. and at pressures between 10 and 50 atmospheres gauge for a period of from about 0.3 to about 6 hours.

6. The process of claim 1, wherein the oxidation catalyst is a cobalt catalyst, a manganese catalyst, or a mixed cobalt and manganese catalyst.

* * * * *